US006203786B1

(12) United States Patent
Teale et al.

(10) Patent No.: US 6,203,786 B1
(45) Date of Patent: Mar. 20, 2001

(54) PINE SHOOT BEETLE ATTRACTANT COMPOSITIONS

(75) Inventors: Stephen A. Teale, Fabius; Dariusz Czokajlo; Francis X. Webster, both of Syracuse, all of NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/113,702

(22) Filed: Jul. 10, 1998

(51) Int. Cl.$^7$ .................................................. A01N 25/00
(52) U.S. Cl. .......................... 424/84; 424/408; 424/409
(58) Field of Search ...................... 424/400, 489, 424/405, 403, 408, 409, 84; 514/456

(56) References Cited

U.S. PATENT DOCUMENTS 4,839,383 * 6/1989 Vite ....................................... 514/456

OTHER PUBLICATIONS

Bouhot, et al., "Spatial and Temporal Distribution of Attacks by *Tomicus piniperda* L. and *Ips Sexdentatus* Boern (Col., Scolytidae) on *Pinus Sylvertris*," *J. Appl. Ent.*, vol. 106, pp. 356–371, 1988.
Byers, J.A., et al., "Olfactory Recognition of Host–Tree Susceptibility by Pine Shoot Beetles," *Naturwissenschaften*, vol. 72, S.324, 1985.
Byers, J.A., et al, "Chemical Ecology of Bark Beetles," *Experientia*, vol. 45, pp. 271–283, 1989.
Byers, J.A., "Simulation of the Mate–Finding Behavior of Pine Shoot Beetles, *Tomicus Piniperda*," *Animal Behavior,* vol. 41, pp. 649–660, 1991.
Byers, J.A., "Attraction of Bark Beetles, *Tomicus Piniperda, Hylurgops Palliatus,* and *Trypodendron Domesticum* and Other Insects to Short–Chain Alcohols and Monoterpenes," *Journal of Chemical Ecology,* vol. 18, No. 12, pp. 2385–2401, 1992.
Chararas, C., et al., "Preference of Certain Scolytidae for Different Confifers: A Statistical Approach," *Journal of Chemical Ecology,* vol. 8, No. 8, pp. 1093–1109, 1982.
Guerrero, A., et al., "Semiochemically Induced Inhibition of Behaviour of *Tomicus Destruens,* " *Naturwissenschaften,* vol. 84, pp. 155–157, 1997.
Kangas, E., et al., "Responses of Blastophagus Piniperda L. (Col, Scolytidae) to Trans–Verbenol, Cis–Verbenol and Verbenone, Known to be Population Pheromones of Some American Bark Beetles," *Ann. Ent. Fenn.,* vol. 36, No. 2, pp. 75–83, 1970.
Lanne, B.S., et al., "Differences in Attraction to Semiochemicals Present in Sympatric Pine Shoot Beetles," *Journal of Chemical Ecology,* vol. 13, No. 5, pp. 1045–1067, 1987.
Löyttyniemi, K., et al., "No Evidence of Population Pheromone in *Tomicus Piniperda* (Coleoptera, Scolytidae): A Field Experiment," *Annales Entomologici Fennici,* vol. 54, pp. 93–95, 1988.

(List continued on next page.)

*Primary Examiner*—Thurman K. Page
*Assistant Examiner*—Liliana Di Nola-Baron
(74) *Attorney, Agent, or Firm*—Heslin & Rothenberg, P.C.

(57) ABSTRACT

Compositions of α-pinene in combination with at least one of α-pinene oxide, myrtenol and nonanal are disclosed. In a preferred embodiment, the composition containing α-pinene and α-pinene oxide may additionally include trans-verbenol. A lure for *Tomicus piniperda* is made up of one or more release devices which dispense α-pinene and at least one of α-pinene oxide, myrtlenol nonanal and trans-verbenol. A method for attracting pine shoot beetles, *Tomicus piniperda*, uses the composition disclosed, optionally as part of a trap.

18 Claims, 3 Drawing Sheets

Number of Beetles Trapped Using Compounds of Example 1 as a Lure

OTHER PUBLICATIONS

Niemeyer, et al., "Field Investigations into the Attraction of *Tomicus Piniperda* to Monoperenes and Enthanol," *J. Appl. Ent.,* vol. 120, pp. 265–267, 1996.

Oksanen, H., et al., "Studies of the Chemical Factors Involved in the Olfactory Orientation of Blastophagus Piniperda (Coleoptera: Scolytidae)," *Proceedings of the Boyce Thompson Institute,* pp. 299–304, 1971.

Perttunen, V., et al., "Aspects of the External and Internal Factors Affecting the Olfactory Orientation of Blastophagus Piniperda," *Proceedings of the Boyce Thompson Institute,* pp. 293–297, 1971.

Schlyter, F., et al., "Reduction of Attack Density of the Bark Beetles *Ips Typographus* and *Tomicus Piniperda* on Host Bark by Verbenone Inhibition of Attraction to Pheromone and Host Kairomone," *Animal Behavior,* pp. 53–68, 1990.

Schroeder, L.M., "Attraction of the Bark Beetle *Tomicus Piniperda* and Some Other Bark–and Wood–Living Beetles to the Host Volatiles α–Pinene and Ethanol," *Entomol. Exp. Appl.,* vol. 46, pp. 203–210, 1988.

Schroeder, L.M., et al., "Attraction of Scolytids and Associated Beetles by Different Absolute Amounts and Proportions of α–pinene and Ethanol," *Journal of Chemical Ecology,* vol. 15, No. 3, pp. 807–817, 1989.

Volz, H–A., "Monoterpenes Governing Host Selections inthe Bark Beetles *Hylurgops Palliatus* and *Tomicus Piniperda,* " *Entomol. Exp. Appl.,* vol. 47, pp. 31–35, 1988.

* cited by examiner

PINE SHOOT BEETLE ATTRACTANT COMPOSITIONS

STATEMENT AS TO THE RIGHTS UNDER FEDERALLY SPONSORED RESEARCH

This invention was made with support from the United States Department of Agriculture under McIntire-Stennis Grant No. 95-81000304CA (210-L109B), Forest Service Grant Nos. 29-9355 (210-6514A) and 23-9541 (210-6540A), and Animal and Plant Health Inspection Service Grant No. 95-81000304CA (210-1414A). The United States government may have rights in the invention.

FIELD OF THE INVENTION

The invention relates to attractants for pine shoot beetles.

BACKGROUND OF THE INVENTION

The pine shoot beetle, *Tomicus piniperda*, (L.) (Coleoptera, Scolytidae), is one of the most destructive insect pests affecting pines in its native range of Europe and Asia. In July of 1992, *Tomicus piniperda* was detected in Ohio, and by July of 1995, surveys showed that eight states (Michigan, Illinois, Indiana, Ohio, Pennsylvania, New York, Wisconsin and Maryland) and southern Ontario were infested. In Europe, *Tomicus piniperda* attacks Scots pine, *Pinus sylvestris*, but recent work in the U.S. has shown that it will shoot feed and breed in at least twelve species of hard and soft pines. Studies conducted in China demonstrated that this beetle has damaged eight pine species and caused serious economic losses in large areas of pine forest. In Sweden, the pine shoot beetle can cause 20% to 45% loss in yearly increment. In Poland, a loss of 36% in yearly increment was reported. A heavily infested Scots pine stand near Lockport, New York, has been experiencing 40%–60% loss in yearly increment since 1982. There is potential for significant economic damage by this insect in North America as well as continued losses in the Palearctic region.

*Tomicus piniperda* is a monogamous bark beetle species. It breeds in the cortical tissue of freshly cut or fallen timber, or very weakened trees. The mating season lasts for four to ten days in late March or early April in upstate New York. Females, which initiate host colonization, establish longitudinal galleries where they oviposit about 100–200 eggs. Development from the egg through the pupal stage lasts about two months. New adults emerge and fly to the tops of tree crowns where they mine and feed in the lateral shoots during the summer and early fall to become sexually mature. Each beetle can damage one to six shoots. Damaged shoots usually break and fall to the ground. After the first ground frost, in October or November, beetles exit the shoots and burrow under the bark at the base of healthy trees where they over winter. In milder climatic conditions some beetles overwinter in the shoots. In spring, soon after the snow melts around tree bases and the air temperature exceeds 10° C., adult beetles start their breeding season. *Tomicus piniperda* normally have one generation per year, but 20% to 80% of beetles (depending on climatic conditions and food availability) can establish two broods that are separated by a short period of shoot feeding.

There has been considerable interest in the possible existence of an aggregation pheromone in *Tomicus piniperda* due to the economic significance of the insect. However, until now, field studies have failed to demonstrate its occurrence. It has been hypothesized that this species uses host volatiles to locate breeding substrate. The literature indicates that *Tomicus piniperda* is attracted to several monoterpenes isolated from Scots pine: $\alpha$-pinene, 3-carene, and terpinolene. A synergistic effect of ethanol with the host monoterpenes has also been reported. Unfortunately, host compounds used as mass trapping lures have not been very effective. Therefore, there is a need for an attractant for *Tomicus piniperda* which is more effective than host compounds.

SUMMARY OF THE INVENTION

The present invention is directed to compositions which display increased attraction for the pine shoot beetle compared to $\alpha$-pinene, a host monoterpene. The compositions are made up of $\alpha$-pinene and a compound chosen from the group consisting of myrtenol, nonanal and $\alpha$-pinene oxide. A composition containing $\alpha$-pinene oxide may additionally contain trans-verbenol.

In another aspect, the invention relates to a lure for *Tomicus piniperda* which is made up of one or more devices for the controlled release of $\alpha$-pinene and one or more compounds chosen from myrtenol, nonanal, $\alpha$-pinene oxide and trans-verbenol.

In still another aspect, the invention relates to a method of attracting pine shoot beetles, comprising providing the lure described above. The invention further relates to a trap for pine shoot beetles, which includes the lure described above, a means of directing beetles to a collecting area and a collection means.

DETAILED DESCRIPTION OF THE INVENTION

The compounds which exhibit a synergistic effect with $\alpha$-pinene, a host terpenoid, in attracting *Tomicus piniperda* are trans-verbenol, $\alpha$-pinene oxide, myrtenol and nonanal. A combination of $\alpha$-pinene and one or more of these compounds may be used as bait to attract the beetles to a trap, or to a point where they can be destroyed by an insecticide. Trapping also serves as a survey means of timing the application of chemical pesticides. Another use for the attractant is to disrupt mating, whereby the beetle population is suppressed by subverting and or interrupting the natural mating and reproduction process. The source and purity of each compound are listed below in Table 1, along with its IUPAC chemical name.

TABLE 1

| Common Name | IUPAC Name | Source & Chemical Purity |
|---|---|---|
| α-Pinene | 2,6,6-Trimethylbicyclo [3.1.1]-hept-2-ene | Aldrich Chem. Co. 98% |
| α-Pinene Oxide | 2,7,7-Trimethyl-3-oxatricyclo- [4.1.1.0$^{2,4}$]octane | Aldrich Chem. Co. 97% |
| trans-Verbenol | trans-4,6,6-Trimethylbicyclo[3.1.1] hept-3-en-2-ol | Phero-Tech Inc. 85% |
| (−) Myrtenol | 6,6-Dimethylbicyclo[3.1.1]hept-2-ene-2-methanol | Aldrich Chem. Co. 95% |
| Nonanal | Nonyl aldehyde | Aldrich Chem. Co. 95% |

The attractant composition contains α-pinene, and α-pinene oxide, myrtenol or nonanal. A composition of α-pinene and α-pinene oxide may additionally contain trans-verbenol. Preferably, the attractant is a two-, or three-component composition: α-pinene and α-pinene oxide; α-pinene and myrtenol; α-pinene and nonanal; or α-pinene, α-pinene oxide and trans-verbenol.

The composition may additionally comprise a carrier solvent. A suitable solvent is one in which all components of a blend are soluble. The solvent may additionally serve to attract beetles, as in the case of ethanol, or to alter the volatility of one or more components of the composition. Exemplary solvents are 1,3-butanediol, methanol, ethanol, n-propanol, isopropanol, 1-butanol, 2-butanol, t-butanol, cyclohexane, isopropyl acetate, ethoxyethanol, ethylene glycol monomethyl ether, low molecular weight polyethylene glycol and polydimethylsiloxane fluid.

The components of the composition may be blended prior to incorporation into a single release device or may be contained in individual devices. Where it is desirable to supply the components separately, one or more devices are combined in a lure. With this method, the composition of the invention is present in the vapor phase as a mixture of the components.

A lure for the pine shoot beetle is made up of one or more devices for releasing the attractant. The attractant is composed of α-pinene and one or more compounds chosen from myrtenol, nonanal, α-pinene oxide and trans-verbenol.

The delivery of pheromones as insect attractants is not effective unless the rate of delivery is within certain very narrow limits. A delivery device must accomplish this discharge of the pheromone to the atmosphere at a specific rate peculiar to the beetle, and for whatever period of time the adults are active in mating. Therefore, it is necessary that the pheromone compound contained in the dispenser be emitted to the atmosphere at a constant rate over a sufficiently long period of field exposure.

Various types of devices for the controlled release of insect attractants are known in the art. Polymer matrices impregnated with an attractant are described in U.S. Pat. Nos. 4,908,208 and 5,008,315 to Dow Corning Co. A laminate of such a matrix with a polymer which is permeable to the chemical attractant is disclosed in U.S. Pat. No. 4,639,393 to Herculite Protective Fabrics. A reservoir device with a capillary-type release mechanism is exemplified by U.S. Pat. No. 4,017,030 to Albany International Co. Devices which incorporate a reservoir and a semipermeable membrane, described in U.S. Pat. Nos. 4,793,555 Dow Corning Co. and 5,750,129 to Phero Tech Inc. are preferred means of releasing the composition of the invention. The disclosures of U.S. Pat. Nos. 4,908,208; 5,008,315; 4,639,393; 4,017,030; 4,793,555 and 5,750,129 are incorporated herein by reference.

The release mechanism should be adjusted so that the components are released at the following rates:

TABLE 2

| Compound | Release Rate (mg/day) |
|---|---|
| α-pinene | 3–600 |
| trans-verbenol | 0.05–10 |
| myrtenol | 0.01–3 |
| α-pinene oxide | 0.05–50 |
| nonanal | 0.005–0.1 |

Release rate is a function of many factors, which are specific to the type of device employed. These factors include, for polymer matrices, the shape of the device and the capacity of the polymer to hold the chemical; for systems incorporating a semipermeable membrane, the porosity or permeability of the membrane, both related to the composition of the polymer and of the attractant chemical; and for reservoir systems, the surface area of any liquid exposed and surface area of an orifice, if any. These factors may be varied to affect the release rate by methods known in the art.

A trap for *Tomicus piniperda* includes the lure of the invention. In addition to a lure, a trap may incorporate a means of directing the beetles to a collecting area and a means of collecting and containing the beetles captured. Exemplary types of traps suitable for use with *Tomicus piniperda* are Lindgren funnel traps (Lindgren, Can. J. Entomol. 115: 299–302, 1983) flight barrier traps (Schroeder, Entomol. Exp. Appl. 46:203–210, 1988), window/barrier traps (Byers, et al., Experientia, 45: 271–283, 1989) and pipe traps with funnel (Byers et al., J. Chem. Ecol., 14: 199–212, 1983), the disclosures of which are incorporated herein by reference. Other means of trapping are well known in the art.

EXPERIMENTAL

Volatiles from beetle infested Scots pine and host volatiles were analyzed by coupled gas chromatography-electroantennography (GC-EAD) to isolate compounds which were detectable by the antenna of *T. piniperda*. The compounds were identified by comparison of mass spectra with a computer mass spectra library. All compounds identified as detectable were tested in a field trapping experiment, alone and in combination with α-pinene. The experiments in Examples 1–4 were performed in a 35-year-old Scots pine stand in western New York in April; the trapping of beetles for experiment 5 took place in Michigan.

Release rates and release devices for the compounds tested are shown in Tables 3 and 4. Release rates were determined in the laboratory at 20° C. The compounds were either contained in and released from individual vials or blended beforehand and released from a single vial as a mixture. The particular method used is noted in the associated table.

The traps used were Lindgren funnel traps and were spaced at a minimum distance of 15 meters. Traps were hung so the collection cups were about 30 cm above the ground. The number of beetles trapped was analyzed statistically.

Chemicals were used as obtained from the suppliers listed in Table 1, except for Example 5, where trans-verbenol was purified as noted. The trans-verbenol supplied by Phero-tech contained about 13% cis-verbenol; the trans-component was a mixture of the (+) and (−) enantiomers. In Examples 1, 2 and 3, the racemic mixture consisted of 77% (−) stereoisomer and 23% (+) stereoisomer; in Example 5, the trans-verbenol mixture contained 81% of the (−) isomer and 19% of the (+) isomer.

TABLE 3

| Compound | Treatment | Release Device & Mix # | Approximate Release Rate (mg/day) |
|---|---|---|---|
| α-Pinene | B | Glass vial, 2.0 ml, open; single compound | 30 |
|  | C | Glass vial, 2.0 ml, open; mix #1 | 25 |
|  | D, F | Glass vial, 2.0 ml, open; mix #2 | 12 |
| β-Pinene | D, F | Glass vial, 2.0 ml, open; mix #2 | 1 |
| Δ-3-Carene | D, F | Glass vial, 2.0 ml, open; mix #2 | 10 |
| Terpinolene | D, F | Glass vial, 2.0 ml, open; mix #2 | 0.6 |
| α-Pinene-oxide | C | Septum vial, 2 ml, with glass tube 20 mm × 2 mm ID; single compound | 2.5 |
|  | D, E, G | Septum vial, 2 ml, with Drummond 10 μl microcapillary glass; single compound | 0.85 |
| Fenchone | D, F | Glass vial, 2.0 ml, open; mix #2 | 0.1 |
| Nonanal | D, F | Glass vial, 2.0 ml, open; mix #2 | 0.05 |
| 4-Thujanol | D, F | Septum vial, 2 ml with glass tube 30 mm × 2 mm ID; mix #3 & 4 | 0.01 |
|  | H | Glass vial, 2 ml, open; single compound | 1.5 |
| trans-Pinene-ol | D, F | Septum vial, 2 ml, with glass tube 30 mm × 2 mm ID; mix #3 & 4 | 0.01 |
| Terpinene-4-ol | D, F | Septum vial, 2 ml, with glass tube 30 mm × 2 mm ID; mix #3 & 4 | 0.15 |
| 4-Allyl anisole | D | Septum vial, 2 ml, with glass tube 30 mm × 2 mm ID; mix #4 | 0.2 |
| trans-Verbenol | C | Glass vial, 2.0 ml, open; mix #1 | 0.2 |
|  | D, F | Septum vial, 2 ml, with glass tube 30 mm × 2 mm ID; mix #3 & 4 | 0.04 |
| Methylacetophenone | D, F | Septum vial, 2 ml, with glass tube 30 mm × 2 mm ID; mix #3 & 4 | 0.15 |
| Myrtenol | D, F | Septum vial, 2 ml, with glass tube 30 mm × 2 mm ID; mix #3 & 4 | 0.01 |
| Carveol | D, F | Septum vial, 2 ml, with glass tube 30 mm × 2 mm ID; mix #3 & 4 | 0.01 |
| p-Cymen-7-ol | D, F | Septum vial, 2 ml, with glass tube 30 mm × 2 mm ID; mix #3 & 4 | 0.01 |
| 3-Hydroxy-3-methyl-2-Butanone | F | SV w/Drummond 10 μ microcapillary glass; Blend #5 | 0.01 |
| 4-Hydroxy-4-methyl-2-Pentanone | F | SV w/ Drummond 10 μ microcapillary glass; Blend #5 | 0.01 |

TABLE 4

| Compound | Treatment | Ex. No. | Release Device* & Dilution | Release Rate (mg/day) |
|---|---|---|---|---|
| α-Pinene | all | 3, 4 | OV; single compound | 30.00 |
| α-Pinene-oxide | C, F | 2 | SV; single compound - high | 0.85 |
|  | D | 4 | SV; single compound - high | 0.85 |
|  | E, H | 2 | SV; 1:10 in BuOH - medium | 0.05 |
|  | C | 4 | SV; 1:10 in BuOH - medium | 0.05 |
|  | B | 3 | SV; 1:10 in BuOH - medium | 0.05 |
|  | C, F | 2 | SV; 1:100 in BuOH - low | 0.005 |
|  | B | 4 | SV; 1:100 in BuOH - low | 0.005 |
| Nonanal | G | 2 | SV; single compound | 0.17 |
| Cis-3-Pinene-2-ol | C | 2 | SV; in blend of @ 20% cis-3-Pinene-2-ol and 40% other compounds | |
|  | B | 3 | V, and 40% other compounds | |

TABLE 4-continued

| Compound | Treatment | Ex. No. | Release Device* & Dilution | Release Rate (mg/day) |
|---|---|---|---|---|
| trans-Verbenol | F, H | 2 | SV; 85% trans-Verbenol and 14% cis-Verbenol 1:10 Butanediol-low | 0.05 |
|  | B | 3 | SV; 85% trans-Verbenol and 14% cis-Verbenol 1:10 Butanediol-low | 0.05 |
| Myrtenol | B, C | 3 | SV; single compound | 0.15 |

*All chemicals were released from 2 ml open vials (OV) or septum vials with Drummond 1 μl micro-capillary glass (SV).

EXAMPLE 1

The experimental design of Example 1 consisted of six replicates with eight treatments randomly assigned with each replicate. An outline of the treatments is given in Table 5. In the Table, the column headed 'Treatment' gives the designation of each different treatment. 'Number of Vials in Treatment' refers to delivery of the chemicals listed in the column labeled 'Content of Vials.' For most of the treatments, more than one compound was tested. In some cases, mixtures of the experimental compounds were prepared. Each mixture and each compound listed was released from its own container.

For example, Treatment A, the control, had no chemical lure; Treatment B consisted of one vial containing α-pinene. Treatment C was released from two vials, one containing a mixture of 10 parts α-pinene with 1 part trans-verbenol, and one containing only α-pinene oxide. The remaining treatments, D–H, were as indicated in Table 5.

TABLE 5

| Treatment | Number of Vials in Treatment | Content of Vials |
|---|---|---|
| A | 0 | Control |
| B | 1 | α-Pinene |
| C | 2 | Blend #1, α-Pinene-oxide |
| D | 3 | Blend #2 & 3, α-Pinene-oxide |
| E | 3 | Blend #2 & 4, α-Pinene-oxide |
| F | 2 | Blend #5 & 6 |
| G | 1 | a-Pinene-oxide |
| H | 1 | 4-Thujanol |

Blend #1: 100 parts α-pinene and 10 parts trans verbenol
Blend #2 100 parts α-pinene, 10 parts beta-pinene, 100 parts Δ-3-carene, 10 parts terpinolene, 2 parts fenchone, and 2 parts nonanal
Blend #3: Equal parts 4-thujanol, cis-3-pinene-2-ol, terpinene-4-ol, trans-verbenol, methylacetophenone, myrtenol, carveol, p-cymen-7-ol
Blend #4: Equal parts 4-thujanol, cis-3-pinene-2-ol, terpinene-4-ol, 4-allylanisole, trans-verbenol, methylaceto-phenone, myrtenol, carveol, p-cymen-7-ol
Blend #5: Equal parts 3-hydroxy-3-methyl-2-butanone and 4-hydroxy-4-methyl-2-pentanone
Blend #6: Equal parts cis-3-pinene-2-ol, trans-Verbenol and Myrtenol The release devices and the release ratios of the compounds are given in Table 3. For example, for Treatment B, α-pinene was released at the rate of 30.00 mg/day from a 2.0 ml open glass vial. For Treatment C, α-pinene was used as a blend with trans-verbenol, designated Blend #1. The release rate for α-pinene in the blend was 25.00 mg/day from a 2.0 ml open glass vial containing the blend; the release rate for trans-verbenol in the mix was 0.20 mg/day. α-Pinene oxide in Treatment C was released separately from the blend at the rate of 2.5 mg/day. The release rate for α-pinene in Blend #2, used in Treatments D and E, was 12.00 mg/day.

Figure 1:
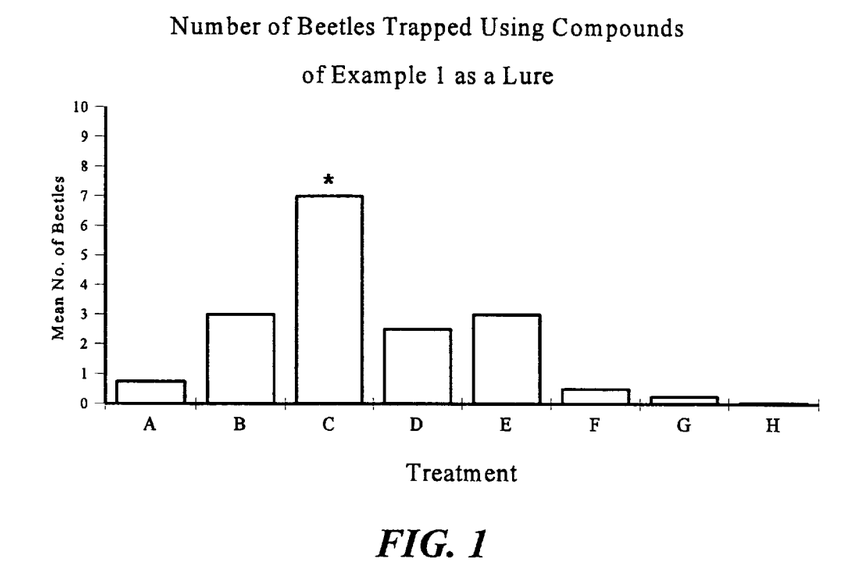
FIG. 1 is a bar graph of the mean number of beetles attracted by various mixtures described in Example 1.

Field trapping revealed a synergistic effect of α-pinene oxide and trans-verbenol, with the host volatile, α-pinene. The results are displayed graphically in FIG. 1. The mean number of beetles captured is charted for each treatment. Each bar corresponds to a treatment in Table 5; the designations of the treatments are listed below the bar. Where a star appears above the bar, the treatment attracted significantly more beetles that the control. FIG. 1 shows that Treatment C, consisting of α-pinene oxide and a blend of α-pinene and trans-verbenol in a 10:1 ratio, attracted about twice as many beetles as Treatment B, containing only α-pinene. Therefore, α-pinene oxide and trans-verbenol synergized the attraction of attraction of the beetles to α-pinene.

EXAMPLE 2

Figure 2:
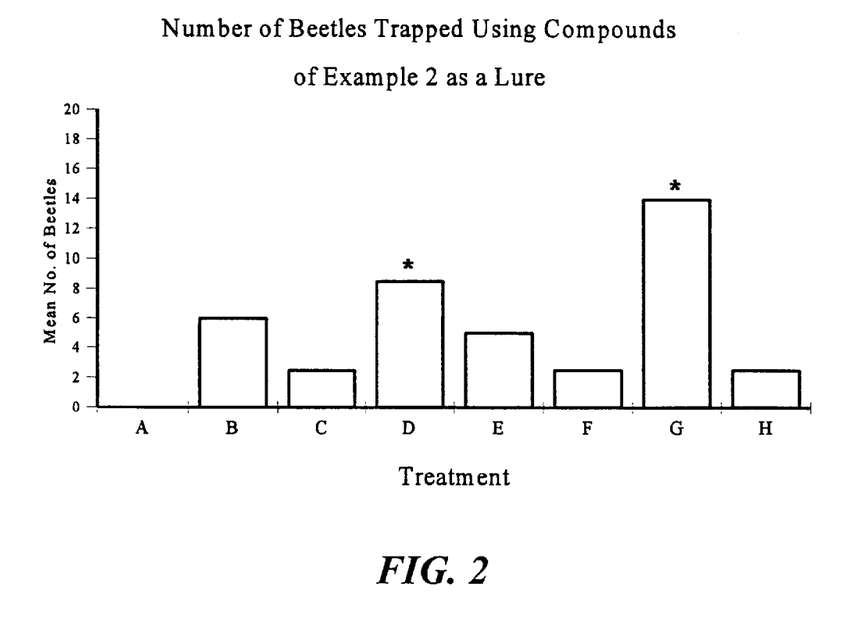
FIG. 2 is a bar graph of the mean number of beetles attracted by various mixtures described in Example 2.

The effect of varying the level of α-pinene oxide in combination with α-pinene and with trans-verbenol in addition to α-pinene was determined. Nonanal was also tested as a synergist with α-pinene. α-Pinene with three graduated levels of α-pinene oxide, and α-pinene/trans-verbenol at low release rate with two levels of α-pinene oxide were evaluated. The composition of the samples tested appear in Table 4. All compounds were released individually from separate vials. The release devices and release rates are given in Table 4. α-Pinene oxide was diluted with 1,3-butanediol in order to reduce the rate of release from the trap. A dilution ratio of 1:10 and 1:100 (α-pinene oxide: 1,3-butanediol) was used for the samples with medium and low levels of α-pinene oxide, respectively and a 1:10 ratio of trans-verbenol to 1,3 butanediol. Results are displayed graphically in FIG. 2. The figure shows that α-pinene oxide at the medium release rate and nonanal, tested separately, synergized *Tomicus piniperda* attraction to α-pinene. It was subsequently discovered that the trans-verbenol used contained about 13% cis-verbenol as a contaminant. The lack of synergism in the samples containing trans-verbenol can be explained by the presence of the contaminant and too low a release rate. Cis-verbenol has previously been reported as an inhibitor of *Tomicus piniperda*.

TABLE 6

| Treatment | Number of Vials in Treatment | Lure Content |
| --- | --- | --- |
| A | — | Control |
| B | 1 | α-Pinene |
| C | 2 | α-Pinene; α-Pinene-oxide - low |
| D | 2 | α-Pinene; α-Pinene-oxide - medium |
| E | 2 | α-Pinene; α-Pinene-oxide - high |
| F | 3 | α-Pinene; a-Pinene-oxide - low trans-Verbenol - low |
| G | 2 | α-Pinene/Nonanal |
| H | 3 | α-Pinene; α-Pinene-oxide - high, trans-Verbenol - low |

Figure 3:
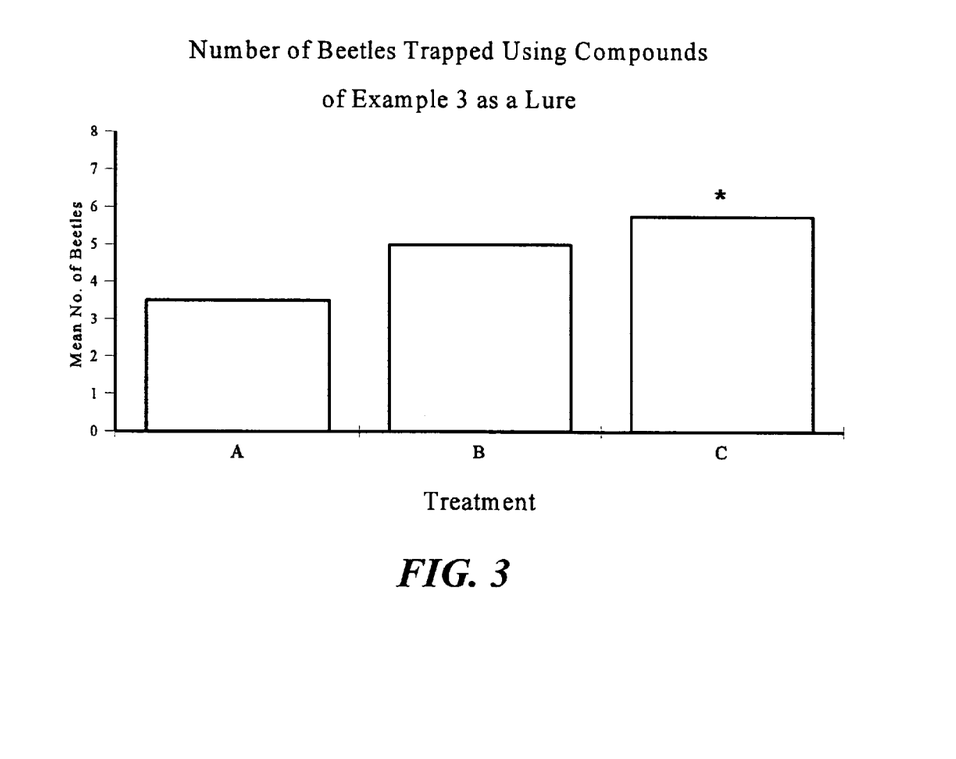
FIG. 3 is a bar graph of the mean number of beetles attracted by various mixtures described in Example 3.

EXAMPLE 3

α-Pinene was also tested with myrtenol, and in combination with four other compounds, α-pinene oxide, trans-verbenol, myrtenol, and cis-3-pinen-2-ol (Table 7). For sample B, all compounds were released from individual vials. Release devices and rates are given in Table 4. α-Pinene was released from a commercial lure for *Tomicus piniperda* sold by Phero-Tech, Inc., British Columbia. The results appear in FIG. 3. It was found that the sample containing myrtenol attracted significantly more beetles than α-pinene alone or in combination with the other compounds.

TABLE 7

| Treatment | Number of Vials in Treatment | Lure Content |
| --- | --- | --- |
| A | 1 | α- Pinene |
| B | 5 | α-Pinene α-Pinene oxide - medium Cis-Pinene-ol trans-Verbenol - low Myrtenol |
| C | 2 | α-Pinene Myrtenol |

EXAMPLE 4

Figure 4:
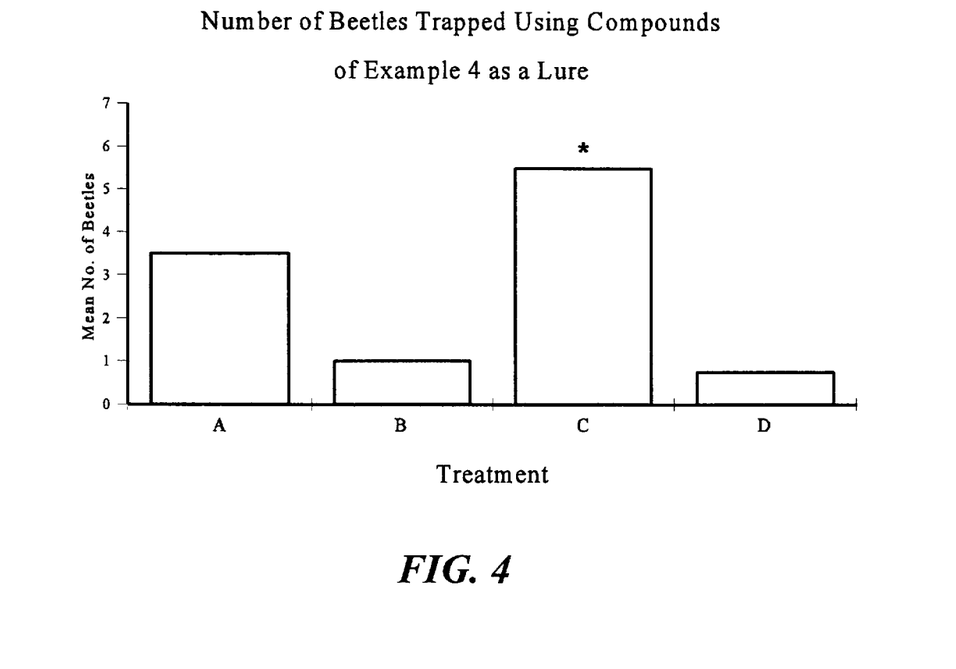
FIG. 4 is a bar graph of the mean number of beetles attracted by various mixtures described in Example 4.

The synergism of *Tomicus piniperda* attraction to host tree volatiles by α-pinene or α-pinene oxide at low, medium and high release rates was tested using baited trap-logs. Sample A is the α-pinene control, and samples B–D are composed of α-pinene with α-pinene oxide at low, medium and high levels, respectively. The release devices and release rates are given in Table 4. Billets baited with α-pinene oxide released at a medium rate attracted significantly more females establishing galleries than billets baited with α-pinene alone. Logs baited with α-pinene oxide released at low and high rates attracted significantly fewer beetles than billets baited with α-pinene alone and α-pinene oxide released at medium rates. These results are displayed graphically in FIG. 4.

EXAMPLE 5

α-Pinene was tested in combination with several components, including a sample of trans-verbenol containing less than 3% of the cis-isomer. The trans-verbenol samples obtained from Phero-tech were contaminated with approximately 16% of the cis-isomer. The material was purified by column chromatography. The experimental design is shown in Table 8; release rates and devices are shown in Table 4. α-Pinene was released from a commercial lure for *Tomicus piniperda* sold by Phero-Tech, Inc., British Columbia. All compounds were released separately from individual devices. Results are displayed graphically in FIG. 5.

Figure 5:
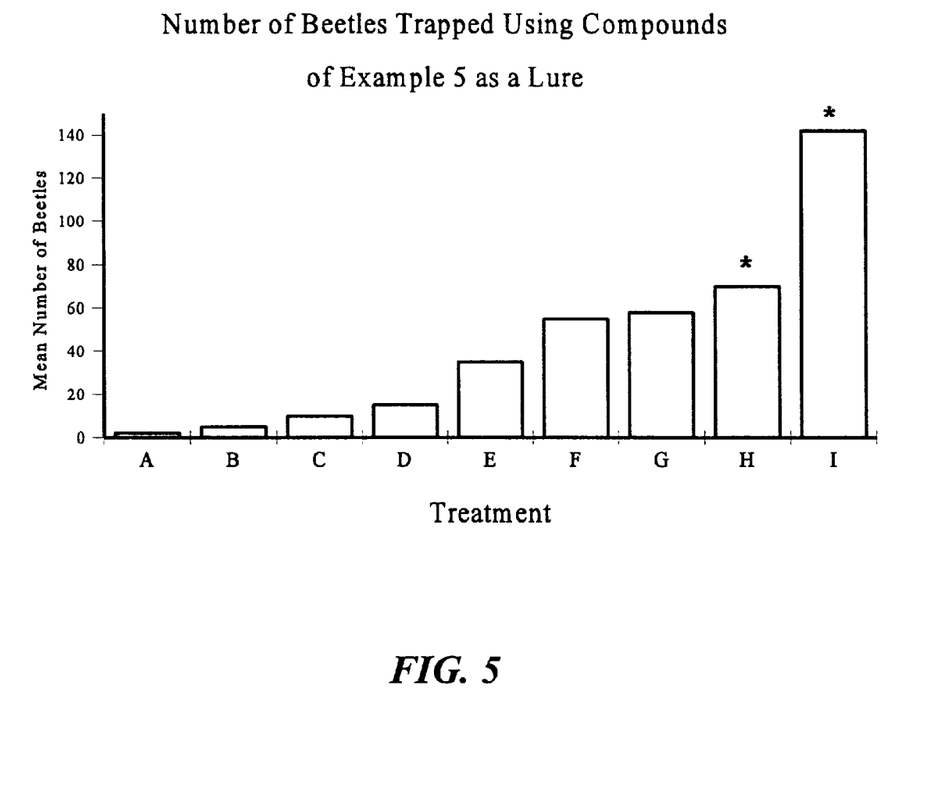
FIG. 5 is a bar graph of the mean number of beetles attracted by various mixtures described in Example 5.

The figure shows that both myrtenol and trans-verbenol increase the attraction of α-pinene to the pine shoot beetle. A combination of myrtenol and α-pinene attracted about twice as many beetles as α-pinene alone. Simultaneous release of trans-verbenol and α-pinene attracted about four times as many beetles to the trap as α-pinene alone.

TABLE 8

| TREATMENT | LURE CONTENT |
| --- | --- |
| A | NONE - Control |
| B | α-pinene, 4-allyl anisole |
| C | α-pinene, 4-Thujanol |
| D | α-pinene, Terpinene-4-ol |
| E | α-pinene |
| F | α-pinene, 3-Hydroxy-3-methyl-2-butanone |
| G | α-pinene, 4-hydroxy-4-methyl-2-pentanone |
| H | α-pinene, Myrtenol |
| I | α-pinene, trans-verbenol |

We claim:

1. A composition for attracting *Tomicus piniperda* comprising α-pinene, trans-verbenol and at least one compound chosen from the group consisting of myrtenol, nonanal, and α-pinene oxide, in a combined amount that is effective to attract *Tomicus piniperda*.

2. A composition according to claim 1, comprising α-pinene, trans-verbenol and myrtenol.

3. A composition according to claim 1, comprising α-pinene, trans-verbenol and nonanal.

4. A composition according to claim 1, comprising α-pinene, trans-verbenol and α-pinene oxide.

5. A composition according to claim 1, additionally comprising a carrier solvent.

6. A composition for attracting *Tomicus piniperda* consisting essentially of α-pinene, trans-verbenol and at least one compound chosen from the group consisting of myrtenol, nonanal, and α-pinene oxide, in a combined amount that is effective to attract *Tomicus piniperda*.

7. A composition according to claim 6, additionally consisting of a carrier solvent.

8. A lure for *Tomicus piniperda* comprising one or more controlled release devices for dispensing α-pinene trans-verbenol and at least one compound chosen from the group consisting of myrtenol, nonanal, and α-pinene oxide in a combined amount that is effective to attract *Tomicus piniperda*.

9. A lure according to claim 8, wherein α-pinene is released at a rate of 3–600 mg/day, myrtenol is released at a rate of 0.01–3.0 mg/day, nonanal is released at a rate of 0.005–0.17 mg/day, α-pinene oxide is released at a rate of 0.05–50 mg/day and trans-verbenol is released at a rate of 0.05–10 mg/day at 20° C. and 1 atm.

10. A lure according to claim 8, wherein α-pinene is released at a rate of about 30 mg/day, myrtenol is released at a rate of about 0.15 mg/day, nonanal is released at the rate of about 0.17 mg/day, α-pinene oxide is released at a rate of about 0.85–2.5 mg/day, and trans-verbenol is released at a rate of about 0.5 mg/day at 20° C. and 1 atm.

11. A method of attracting pine shoot beetles, *Tomicus piniperda*, comprising the controlled release of α-pinene, trans-verbenol and at least one compound chosen from the group consisting of myrtenol, nonanal, α-pinene oxide and trans-verbenol in a combined amount effective to attract *Tomicus piniperda*.

12. The method of claim 11, wherein α-pinene, trans-verbenol and myrtenol are released.

13. The method according to claim 11, wherein α-pinene, trans-verbenol and nonanal are released.

14. The method according to claim 11, wherein α-pinene trans-verbenol and α-pinene oxide are released.

15. The method of claim 11, wherein a carrier solvent is additionally released.

16. The method of claim 11, additionally comprising providing a trap for *Tomicius piniperda*.

17. A trap for pine shoot beetles, *Tomicus piniperda*, comprising the lure of claim 8, a means of directing said beetles to a collecting area and a collection means.

18. A lure according to claim 8, wherein α-pinene is released at a rate of 3 to 600 mg/day, myrtenol is released at a rate of 0.01 to 10 mg/day, nonanal is released at a rate of 0.05 to 10 mg/day, α-pinene oxide is released at a rate of 0.05 to 50 mg/day and trans-verbenol is released at a rate of 0.05 to 10 mg/day at 20° C. and 1 atm.

* * * * *

UNITED STATES PATENT AND TRADEMARK OFFICE
CERTIFICATE OF CORRECTION

PATENT NO. : 6,203,786 B1 Page 1 of 1
DATED : March 20, 2001
INVENTOR(S) : Stephen A. Teale, Dariusz Czokajlo, and Francis X. Webster It is certified that error appears in the above-identified patent and that said Letters Patent is hereby corrected as shown below:

<u>Column 1,</u>
Line 10, change "29-9355" to -- 23-9355 --.

Signed and Sealed this

Thirtieth Day of October, 2001

Attest:

*Nicholas P. Godici*

NICHOLAS P. GODICI
*Attesting Officer*     *Acting Director of the United States Patent and Trademark Office*